US012656308B2

(12) United States Patent
Kawamoto et al.

(10) Patent No.: US 12,656,308 B2
(45) Date of Patent: Jun. 16, 2026

(54) GAS CONCENTRATION MEASURING DEVICE AND MANUFACTURING METHOD FOR THE SAME

(71) Applicant: DENSO CORPORATION, Kariya-city (JP)

(72) Inventors: Yusuke Kawamoto, Kariya-city (JP); Yusuke Todo, Kariya-city (JP); Hiroo Imamura, Kariya-city (JP); Mitsunobu Nakato, Kariya-city (JP)

(73) Assignee: DENSO CORPORATION, Kariya-City (JP)

( * ) Notice: Subject to any disclaimer, the term of this patent is extended or adjusted under 35 U.S.C. 154(b) by 884 days.

(21) Appl. No.: 17/110,634

(22) Filed: Dec. 3, 2020

(65) Prior Publication Data

US 2021/0088472 A1      Mar. 25, 2021

Related U.S. Application Data

(63) Continuation of application No. PCT/JP2019/022768, filed on Jun. 7, 2019.

(30) Foreign Application Priority Data

Jun. 8, 2018      (JP) ............................. JP2018-110581

(51) Int. Cl.
*G01N 27/419* (2006.01)
*G01N 27/407* (2006.01)
(Continued)

(52) U.S. Cl.
CPC ....... *G01N 27/419* (2013.01); *G01N 27/4074* (2013.01); *G01N 27/4175* (2013.01); *G01N 33/0016* (2013.01); *G01N 33/0037* (2013.01)

(58) Field of Classification Search
CPC ............. G01N 27/419; G01N 27/4074; G01N 27/4175; G01N 33/0016; G01N 33/0037; Y02A 50/20
See application file for complete search history.

(56) References Cited

U.S. PATENT DOCUMENTS 6,295,862 B1      10/2001      Kurokawa et al.
6,344,134 B1 *      2/2002      Yamada ............... G01N 27/417
73/23.31

(Continued)

FOREIGN PATENT DOCUMENTS

DE      112015005659 T5      8/2017
JP      2004-028925      1/2004

(Continued)

*Primary Examiner* — Shizhi Qian
(74) *Attorney, Agent, or Firm* — Nixon & Vanderhye PC

(57) ABSTRACT

A gas sensor, an oxygen concentration measuring unit, and a computation unit are included. The gas sensor measures a concentration $C_{NOX}$ of specific gas contained in measured gas. The oxygen concentration measuring unit measures a concentration $C_{O2}$ of oxygen in the measured gas outside the gas sensor. The gas sensor has a measured gas chamber, a reference gas chamber, a diffusion resistance unit, a pump cell, and a sensor cell. The computation unit computes a concentration $C_{NOX}$ of the specific gas by using the concentration $C_{O2}$ of oxygen measured by using the oxygen concentration measurement unit and the sensor current.

16 Claims, 9 Drawing Sheets

(51) Int. Cl.
    G01N 27/417      (2006.01)
    G01N 33/00       (2006.01)

(56)            References Cited

U.S. PATENT DOCUMENTS

| | | | | |
|---|---|---|---|---|
| 2001/0039825 | A1 | 11/2001 | Kurokawa et al. | |
| 2002/0130053 | A1* | 9/2002 | Ando | F01N 11/00 |
| | | | | 204/426 |
| 2005/0077177 | A1* | 4/2005 | Sakayanagi | G01N 27/4074 |
| | | | | 204/425 |
| 2009/0114536 | A1* | 5/2009 | Ishiguro | G01N 33/0016 |
| | | | | 204/406 |
| 2009/0242427 | A1* | 10/2009 | Muroguchi | G01N 27/419 |
| | | | | 205/781 |
| 2017/0363570 | A1 | 12/2017 | Sugiura | |

FOREIGN PATENT DOCUMENTS

| | | |
|---|---|---|
| JP | 2007-108018 | 4/2007 |
| JP | 2012-052901 | 3/2012 |

\* cited by examiner

MATERIAL PRODUCTION PROCESS

230

FORMATION PROCESS $26_P'$    $26_S'$    2'

27'

271'

23'

25'

272'

28'

$26_B'$

CALCINATION PROCESS

100

2'

GAS CONCENTRATION MEASURING DEVICE AND MANUFACTURING METHOD FOR THE SAME

CROSS REFERENCE TO RELATED APPLICATION

The present application is a continuation application of International Patent Application No. PCT/JP2019/022768 filed on Jun. 7, 2019, which designated the U.S. and claims the benefit of priority from Japanese Patent Application No. 2018-110581 filed on Jun. 8, 2018. The entire disclosures of all of the above applications are incorporated herein by reference.

TECHNICAL FIELD

The present disclosure relates to a gas concentration measuring device and a method for manufacturing the gas concentration measuring device.

BACKGROUND

Conventionally, a gas sensor is employed for measuring a concentration of specific gas (for example, NOx) contained in measured gas such as exhaust gas.

SUMMARY

According to an aspect of the present disclosure, a gas concentration measuring device includes a gas sensor configured to measure a concentration $C_{NOX}$ of specific gas contained in measured gas; an oxygen concentration measuring unit configured to measure an oxygen concentration $C_{O2}$ in the measured gas; and a computation unit configured to compute a concentration $C_{NOX}$ of the specific gas.

BRIEF DESCRIPTION OF THE DRAWINGS

The above and other objects, features and advantages of the present disclosure will become more apparent from the following detailed description made with reference to the accompanying drawings. In the drawings.

DETAILED DESCRIPTION

Figure 1:
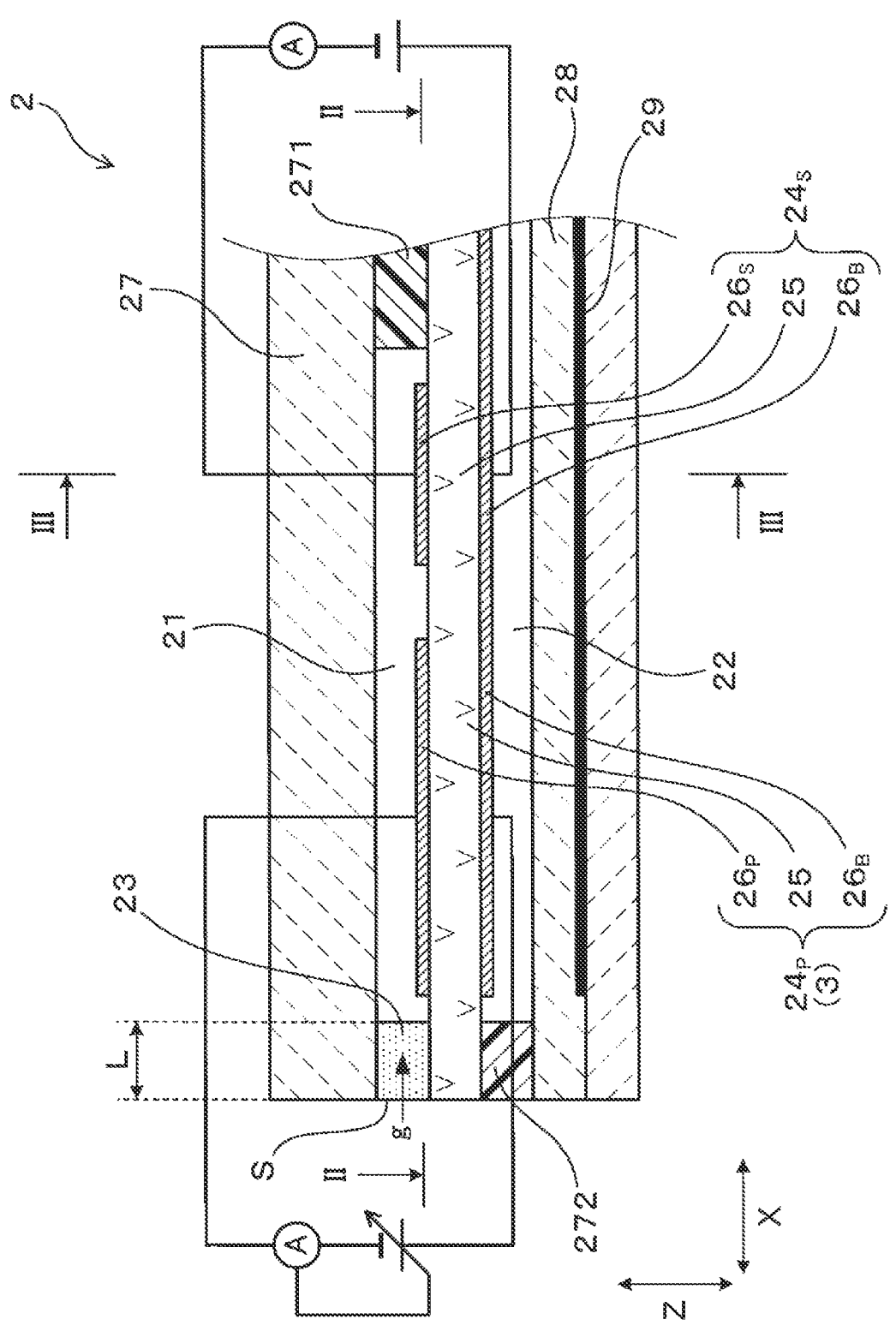
FIG. 1 is a cross-sectional view showing a gas sensor according to a first embodiment.

As follow, examples of the present disclosure will be described.

According to an example of the present disclosure, a gas sensor is configured to measure a concentration of specific gas, such as NOx, contained in measured gas, such as exhaust gas. A gas concentration measuring device includes a computation unit connected to the gas sensor.

According to an example of the present disclosure, the gas sensor has a measured gas chamber into which the measured gas is introduced, a reference gas chamber, into which a reference gas such as atmospheric air is introduced, a pump cell, and a sensor cell. A diffusion resistance portion for controlling a rate of the measured gas is provided at an inlet of the measured gas chamber.

According to an example of the present disclosure, the pump cell includes a solid electrolyte body, a pump electrode formed on a surface of the solid electrolyte body on the side of the measured gas chamber, and a reference electrode formed on a surface of the solid electrolyte body on the side of the reference gas chamber. When a voltage is applied to the pump cell, oxygen is reduced on the pump electrode to generate oxygen ion. The generated oxygen ion is conducted through the solid electrolyte body to move toward the reference electrode and is discharged to the reference gas chamber. The sensor cell includes a solid electrolyte body, a sensor electrode formed on the surface of the solid electrolyte body on the side of the measured gas chamber, and a reference electrode formed on the surface of the solid electrolyte body on the side of the reference gas chamber. A current (sensor current) corresponding to the specific gas concentration in the measured gas chamber flows through the sensor cell. The computation unit computes the specific gas concentration by using the measured value of the sensor current.

The specific gas concentration may not be computed accurately simply by using the measured value of the sensor current. That is, when oxygen is discharged by using the pump cell, the pressure in the measured gas chamber is reduced. Further, the oxygen concentration in the measured gas chamber becomes lower than the concentration outside the gas sensor (that is, inside the exhaust pipe). Therefore, the measured gas newly flows into the measured gas chamber from the outside of the gas sensor. The specific measured gas also includes the specific measured gas, and therefore, the specific gas concentration in the measured gas chamber becomes higher than the external concentration as a result of the inflow. In addition, the oxygen concentration of the measured gas fluctuates. Therefore, when the oxygen concentration is high, the amount of oxygen discharged by using the pump cell increases (that is, the amount of newly flowing measured gas increases). When the oxygen concentration is low, the amount of oxygen discharged by using the pump cell is small (that is, the amount of newly flowing measured gas is small). Therefore, the specific gas concentration in the actual exhaust gas and the specific gas concentration in the measured gas chamber may differ, and the specific gas concentration may not be measured accurately.

According to an example of the present disclosure, a gas concentration measuring device includes: a gas sensor configured to measure a concentration $C_{NOX}$ of specific gas contained in measured gas; an oxygen concentration measuring unit configured to measure an oxygen concentration $C_{O2}$ in the measured gas; and a computation unit configured to compute a concentration $C_{NOX}$ of the specific gas. The gas sensor has a gas chamber configured to be introduced with the measured gas, a reference gas chamber configured to be introduced with the reference gas, a diffusion resistance unit configured to regulate a flow velocity of the measured gas introduced into the measured gas chamber, a pump cell configured to move oxygen from the measured gas chamber to the reference gas chamber, and a sensor cell configured to cause a sensor current I to flow therethrough correspondingly to the concentration $C_{NOX}$ of the specific gas in the measured gas chamber. The computation unit is configured to compute the concentration $C_{NOX}$ of the specific gas by using a measured value of the oxygen concentration $C_{O2}$ with the oxygen concentration measuring unit and a measured value of the sensor current I.

According to this example, the gas concentration measuring device includes the oxygen concentration measuring unit and the computation unit. The oxygen concentration measuring unit measures the oxygen concentration in the measured gas. The computation unit computes the specific gas concentration by using the measured value of the oxygen concentration and the measured value of the current (that is, the sensor current) of the sensor cell.

Therefore, when the specific gas concentration is computed, the information on the oxygen concentration in the measured gas can be reflected. Thus, the specific gas concentration can be accurately acquired without being significantly affected by the oxygen concentration.

As described above, the configuration according to this example may enable to provide the gas concentration measuring device configured to measure the specific gas concentration contained in the measured gas more accurately.

First Embodiment

Figure 5:
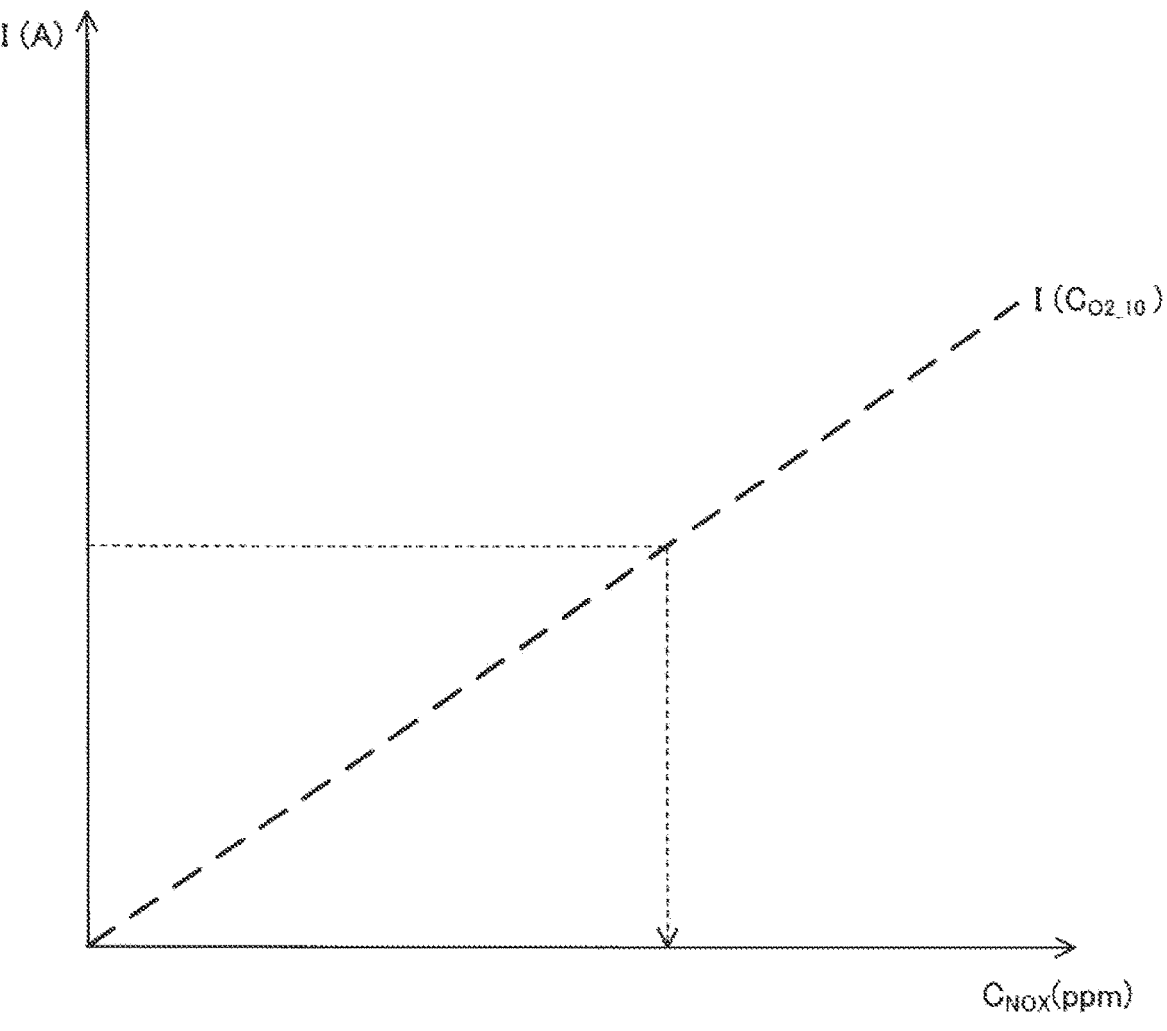
FIG. 5 is a graph showing a relationship between the sensor current I and the specific gas concentration $C_{NOX}$ when the oxygen concentration $C_{O2}$ is 10% according to the first embodiment.
Figure 6:
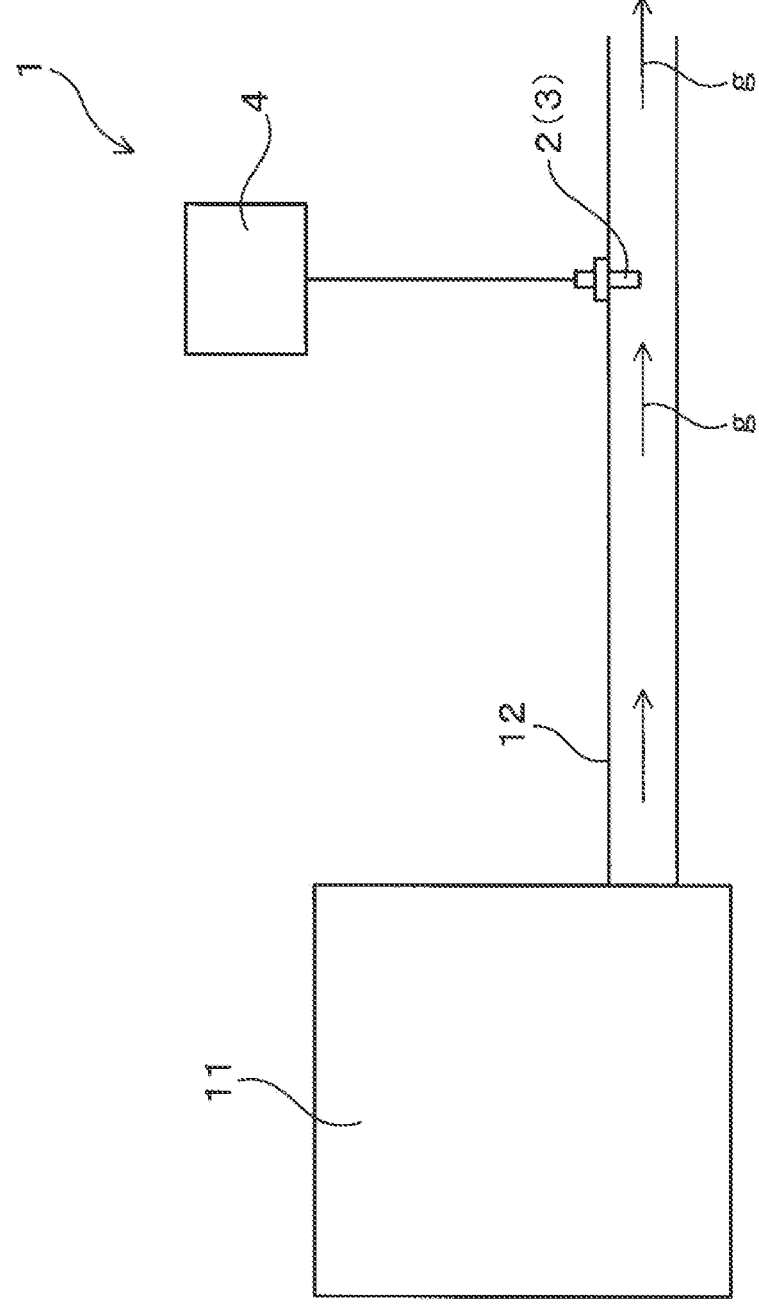
FIG. 6 is a schematic diagram showing a gas concentration measuring device according to the first embodiment.

A gas concentration measuring device according to the first embodiment will be described with reference to FIGS. 1 to 8. As shown in FIG. 6, the gas concentration measuring device 1 of the present embodiment includes a gas sensor 2, an oxygen concentration measuring unit 3, and a computation unit 4. The gas sensor 2 is provided for measuring the concentration $C_{NOX}$ of specific gas contained in measured gas g. The measured gas g in this embodiment is exhaust gas of the engine 11, and the specific gas is NOx. The oxygen concentration measuring unit 3 measures a oxygen concentration $C_{O2}$ in the measured gas g outside the gas sensor 2. In addition, the computation unit 4 computes the concentration $C_{NOX}$ of the specific gas.

Figure 2:
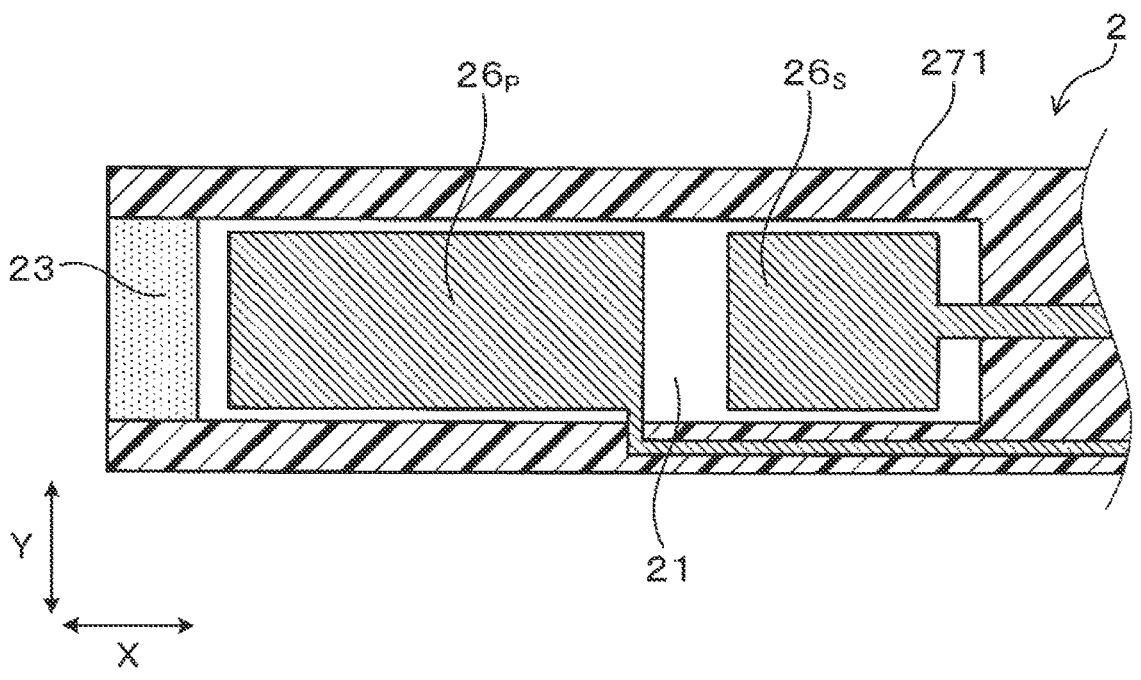
FIG. 2 is a cross-sectional view taken along a line II-II in FIG. 1.
Figure 3:
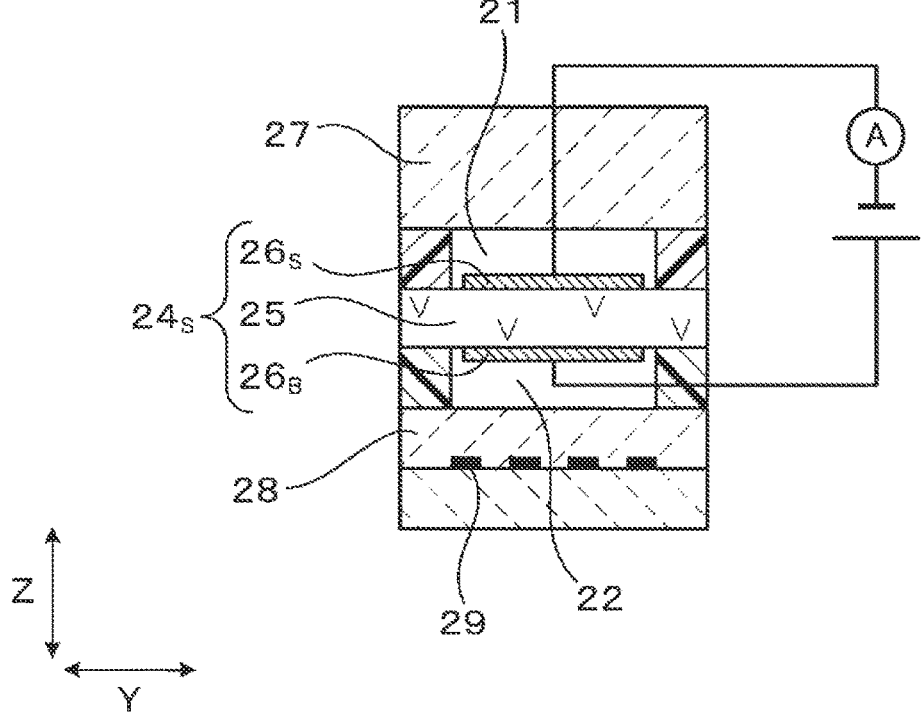
FIG. 3 is a cross sectional view taken along a line III-III in FIG. 1.

As shown in FIGS. 1 to 3, the gas sensor 2 has a measured gas chamber 21, a reference gas chamber 22, a diffusion resistance unit 23, a pump cell $24_P$, and a sensor cell $24_S$. The measured gas g is introduced into the measured gas chamber 21, and the reference gas such as the atmospheric air is introduced into the reference gas chamber 22. The reference gas is gas that serves as a reference of the oxygen concentration. Further, the diffusion resistance portion 23 is made of a porous body such as ceramics. The diffusion resistance unit 23 regulates a flow velocity of the measured gas g introduced into the measured gas chamber 21.

The pump cell 24P discharges oxygen from the measured gas chamber 21 to the reference gas chamber 22. Further, a sensor current I corresponding to the concentration $C_{NOX}$ of the specific gas in the measured gas chamber 21 flows through the sensor cell $24_S$.

The computation unit 4 is configured to compute the concentration $C_{NOX}$ of the specific gas by using the measured value of the oxygen concentration $C_{O2}$ by the oxygen concentration measuring unit 3 and the measured value of the sensor current I. The computation unit 4 is provided in a known sensor control unit. The sensor control unit is electrically connected to the gas sensor 2 with a wire or the like. The sensor control unit includes a sensor control circuit that controls a voltage applied to the sensor cell $24_S$ and a pump cell $24_P$, a heater control circuit that controls a voltage of the heater 29, an arithmetic processing unit that acquires and performs computation on the output from the sensor cell $24_S$ and the output from the pump cell $24_P$, a storage device that stores a computed result and a parameter used in computation, and the like, which will be described later. The computation unit 4 includes the above-mentioned arithmetic processing unit and the storage device.

The gas concentration measuring device 1 of this embodiment is mounted on a vehicle. As shown in FIG. 6, an exhaust pipe 12 is connected to an engine 11 of the vehicle, and a gas sensor 2 is attached to the exhaust pipe 12. The gas sensor 2 is used to measure the concentration $C_{NOX}$ of NOx contained in the exhaust gas.

As shown in FIG. 1, the gas sensor 2 includes a solid electrolyte body 25, multiple insulating plates 27, 28, and partition walls 271, 272. The solid electrolyte body 25 is arranged between the measured gas chamber 21 and the reference gas chamber 22. A pump electrode $26_P$ and a sensor electrode $26_S$ are formed on the surface of the solid electrolyte body 25 on the side of the measured gas chamber 21 in this order from the upstream in the flow direction of the measured gas. A reference electrode 26B is formed on the surface (back surface) of the solid electrolyte body 25 on the side of the reference gas chamber 22. The pump cell $24_P$ includes the pump electrode $26_P$, the solid electrolyte body 25, and the reference electrode 26B. Further, the sensor cell $24_S$ includes the sensor electrode $26_S$, the solid electrolyte body 25, and the reference electrode 26B. In this embodiment, the reference electrode 26B of the pump cell $24_P$ and the reference electrode 26B of the sensor cell $24_S$ are integrated to form one common electrode.

The pump electrode $26_P$ is formed of a porous cermet electrode containing Au and Pt. Further, the sensor electrode 50 is formed of a porous cermet electrode containing Pt and Rh. Further, the solid electrolyte body 25 is made of yttria-stabilized zirconia (YSZ).

An insulating plate 28 is provided on the opposite side of the solid electrolyte body 25 across the reference gas chamber 22 interposed therebetween. A heater 29 is arranged in the insulating plate 28. The insulating plate 28 is formed by laminating two insulating layers, and the heater 29 is formed by forming a heater pattern, which is a heat generation resistance wire, on one of the insulating layers. The heater 29 is used to heat each of the solid electrolyte body 25, the pump cell $24_P$, and the sensor cell $24_S$, and the temperature thereof is controlled at an active temperature (for example, 600° C. or higher) at which the detection function is exhibited. When a voltage is applied to the pump cell $24_P$ in a state where the pump cell $24_P$ is heated and is activated, oxygen contained in the measured gas g becomes oxygen ions at the pump electrode $26_P$, passes through the solid electrolyte body 25, and is discharged to the reference gas chamber 22. By measuring the current flowing at this time, the oxygen concentration in the measured gas g is computed. That is, in this embodiment, the pump cell $24_P$ also serves as the oxygen concentration measuring unit 3 described above.

Further, the measured gas g after discharging oxygen reaches the sensor electrode $26_S$ arranged downstream in the measured gas chamber 21. The specific gas (NOx) in the measured gas g is ionized at the sensor electrode $26_S$ and is discharged to the reference gas chamber 22 through the solid electrolyte body 25. The current flowing at this time (that is, the sensor current I) is measured, and the measured value is used to compute the concentration $C_{NOX}$ of the specific gas.

The sensor electrode $26_S$ is active to both NOx and oxygen. Therefore, oxygen is first discharged by using the pump cell $24_P$ to reduce the oxygen concentration of the measured gas g, and subsequently, the specific gas concentration $C_{NOX}$ is measured. Therefore, the sensor current I is a current that includes not only the current that flows due to the ionization of the specific gas (NOx) but also the current that flows due to the ionized oxygen.

Next, a method of computing the specific gas concentration $C_{NOX}$ by using the computation unit 4 will be described in more detail. The computation unit 4 of this embodiment computes the specific gas concentration $C_{NOX}$ from the following equation (1) by using the oxygen concentration $C_{O2}$ and the sensor current I.

(equation (1))

$$I = A\frac{P}{T}\frac{S}{L}C_{NOX}\left\{D + \frac{1}{\beta}P\ C_{O2}\ln(1 - C_{O2})\right\} \quad (1)$$

In the above equation, S is the area of the diffusion resistance portion 23 in the plane orthogonal to the introduction direction (X direction: see FIG. 1) of the measured gas, and L is the length of the diffusion resistance portion 23 in the X direction. Further, P is pressure of the measured gas g outside the gas sensor 2, T is temperature of the diffusion resistance portion 23, and D is a diffusion coefficient of the measured gas g. Further, A and 13 are constants. More specifically, 13 is a constant determined in dependence upon the material of the diffusion resistance portion 23.

When oxygen is discharged from the measured gas g by using the pump cell 24P, the pressure in the measured gas chamber 21 is lowered. Therefore, the measured gas g newly flows into the measured gas chamber 21 from the outside through the diffusion resistance portion 23 according to the pressure difference. Further, when oxygen is discharged from the measured gas g, a difference in oxygen concentration occurs between the measured gas chamber 21 and the outside. Therefore, the measured gas g newly flows into the measured gas chamber 21 from the outside according to the difference in oxygen concentration. The newly inflowing measured gas g contains the specific gas. Therefore, the specific gas concentration in the measured gas chamber 21 increases. The above equation (1) is obtained by computing the sensor current I in consideration of this increase.

In the above equation (1), the area S, the length L, and the constant β of the diffusion resistance portion 23 are values unique to the gas sensor 2. Although there are variations among the gas sensors 2 in these values S, L, and β, these values S, L, and β do not change after the gas sensor 2 is manufactured. That is, these values S, L, and β may be regarded as constant values. Further, the pressure P has a small influence on the above equation (1), and therefore, the pressure P can be regarded as a constant value in the computation. Further, in the present embodiment, as described above, the heater 29 (see FIG. 1) is used to heat the pump cell 24P and the like, and the temperature is controlled to be constant, so that the temperature T of the diffusion resistance portion 23 is kept substantially constant. Therefore, in the above equation (1), it can be considered that only the specific gas concentration $C_{NOX}$ and the oxygen concentration $C_{O2}$ are variables, and the others are constants. Further, assuming that the oxygen concentration $C_{O2}$ reaches a certain value, the above equation (1) can be considered such that all parameters other than the specific gas concentration $C_{NOX}$ are constant values and can be transformed into the following equation.

$$I = \gamma C_{NOX}$$

That is, when the oxygen concentration $C_{O2}$ takes a constant value, the sensor current I is expressed as a linear function of the specific gas concentration $C_{NOX}$. In this embodiment, the oxygen concentration measuring unit 3 is used to measure the oxygen concentration $C_{O2}$ in the measured gas g, and the measured value is used to compute the inclination γ of the linear function as described later. In this way, the above equation (1) is determined according to the oxygen concentration $C_{O2}$. As shown in FIG. 5, when the above equation (1) can be determined, the specific gas concentration $C_{NOX}$ can be computed from the sensor current I.

Further, as described above, the area S, the length L, and the constant β of the diffusion resistance portion 23 vary among the gas sensors 2. Therefore, in this embodiment, after the gas sensor 2 is manufactured, a calibration process is performed to correct the characteristic variation of the diffusion resistance portion 23. More specifically, in the calibration process, the manufactured gas sensor 2 is exposed to a reference gas having the specific gas concentration $C_{NOX}$ that is a predetermined specific gas reference value $C_{NOX\_S}$ (for example, 2000 ppm) and having the oxygen concentration $C_{O2}$ that is a predetermined oxygen reference value $C_{O2\_S}$ (for example, 0%), and the sensor current I is actually measured.

Figure 4:
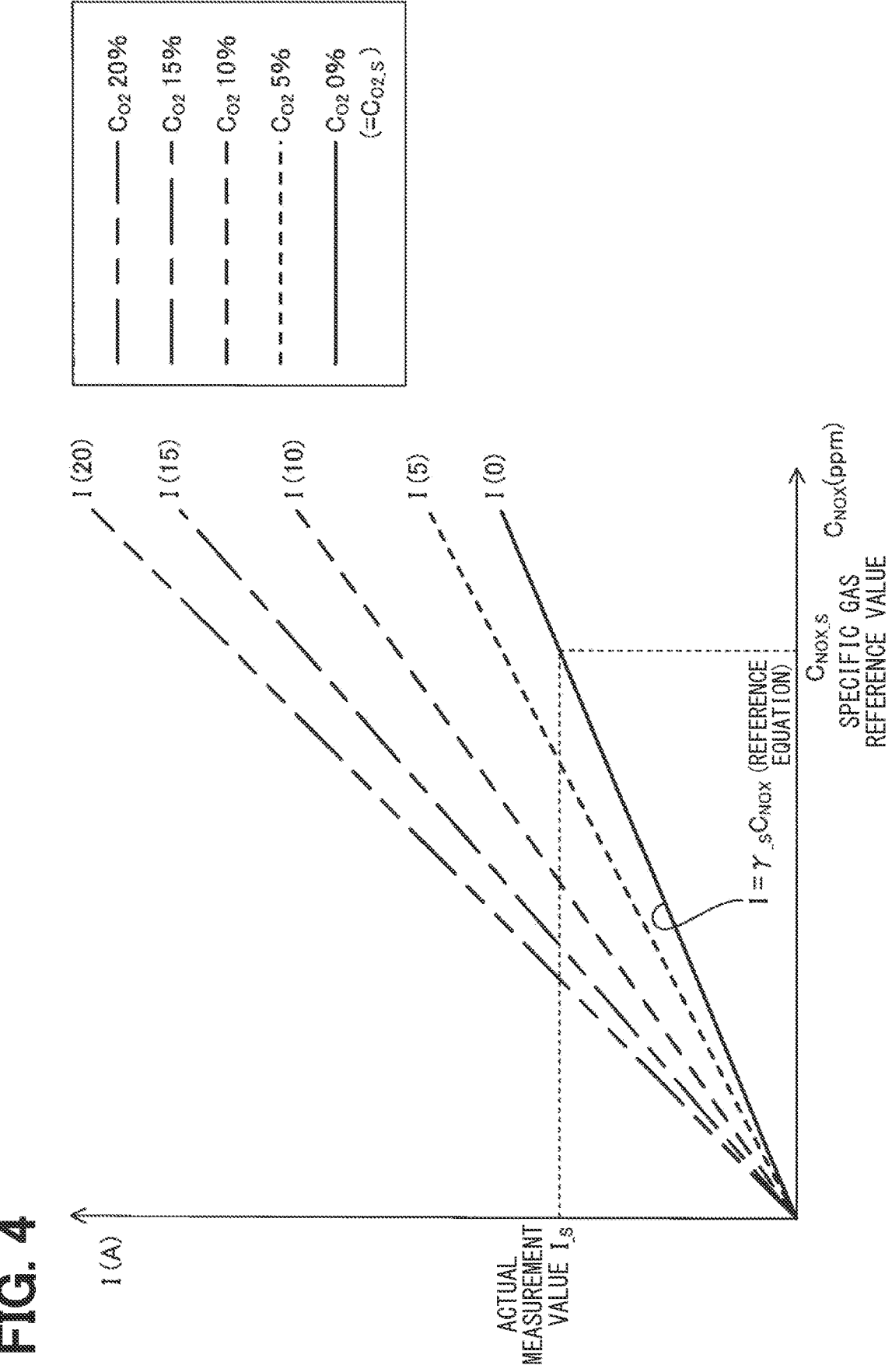
FIG. 4 is a graph showing a relationship between a sensor current I and a specific gas concentration $C_{NOX}$ for each oxygen concentration $C_{O2}$ according to the first embodiment.

As shown in FIG. 4, when the oxygen concentration $C_{O2}$ is constant, the relationship between the sensor current I and the specific gas concentration $C_{NOX}$ is a linear function (that is, the above equation $I = \gamma C_{NOX}$). As the oxygen concentration $C_{O2}$ increases, the inclination γ of the linear function becomes large. In this embodiment, the manufactured gas sensor 2 is exposed to the reference gas, and the sensor current I at that time is actually measured. Subsequently, the computation unit 4 is caused to store the actually measured value $I_S$ of the sensor current I.

When the oxygen concentration $C_{O2}$ is the oxygen reference value $C_{O2\_S}$, the above equation (1) can be expressed by the following equation (2).

(equation (2))

$$I = \gamma_S C_{NOX} \quad (2)$$

$$\gamma_S = \frac{I_S}{C_{NOX\_S}}$$

The characteristics (S, L, β) of the diffusion resistance portion 23 of each gas sensor 2 are all included in the above equation (2). In this embodiment, when the oxygen concentration $C_{O2}$ takes a constant value other than the oxygen reference value $C_{O2\_S}$, the inclination γ of the linear function is computed by using the above equation (2) (hereinafter, also referred to as a reference equation). That is, the inclination γ corresponding to the oxygen concentration $C_{O2}$ measured by using the oxygen concentration measuring unit

3 is computed by using the above reference equation, thereby specifying the above equation (1).

Hereinafter, a method for computing the inclination $\gamma$ when the oxygen concentration $C_{O2}$ is other than the oxygen reference value $C_{O2\_S}$ will be described. The computation unit 4 stores a ratio $n_{\_a}$ of the sensor current I to the above reference equation when the oxygen concentration $C_{O2}$ is a predetermined discrete value $C_{O2\_a}$ other than the oxygen reference value $C_{O2\_S}$. The ratio $n_{\_a}$ can be expressed by the following equation (3).

(equation (3))

$$n_{\_a} = \frac{I(C_{O2\_a})}{I(C_{O2\_S})} \qquad (3)$$

$$= \frac{A\dfrac{P}{T}\dfrac{S}{L}C_{NOX}\left\{D + \dfrac{1}{\beta}PC_{O2\_a}\ln(1 - C_{O2\_a})\right\}}{A\dfrac{P}{T}\dfrac{S}{L}C_{NOX}\left\{D + \dfrac{1}{\beta}PC_{O2\_S}\ln(1 - C_{O2\_S})\right\}}$$

The discrete value $C_{O2\_a}$ and a in the ratio $n_{\_a}$ mean the value of the oxygen concentration $C_{O2}$. The ratio $n_{\_a}$ can be computed in advance and becomes a constant value regardless of the gas sensor 2. That is, it is considered that the ratio $n_{\_a}$ is not affected by a manufacturing variation of the characteristics (S, L, 13, and the like) of the diffusion resistance portion 23 and is a value common to all the gas sensors 2. The computation unit 4 stores this ratio $n_{\_a}$ as a numerical value.

FIG. 4 shows a relationship between the sensor current I and the specific gas concentration $C_{NOX}$ in a case where the oxygen concentration $C_{O2}$ is the oxygen reference value $C_{O2\_S}$ (that is, 0%) and in a case where the oxygen concentration $C_{O2}$ is the discrete value is $C_{O2\_a}$ (5, 10, 15, 20%). As shown in the figure, when the oxygen concentration takes the discrete value $C_{O2\_a}$, the inclination $\gamma$ becomes larger than that of the reference equation. When the oxygen concentration takes the discrete value $C_{O2\_a}$, the above equation (1) can be derived by multiplying the inclination $\gamma_{\_S}$ of the reference equation by the ratio $n_{\_a}$. That is, $$I = n_{\_a}\gamma_{\_S}C_{NOX}$$

can be derived.

The computation unit 4 computes the specific gas concentration $C_{NOX}$ by using the derived equation ($I = n_{\_a}\gamma_{\_S}C_{NOX}$) when the oxygen concentration $C_{O2}$ measured by using the oxygen concentration measuring unit 3 is the above-described discrete value $C_{O2\_a}$.

Figure 7:
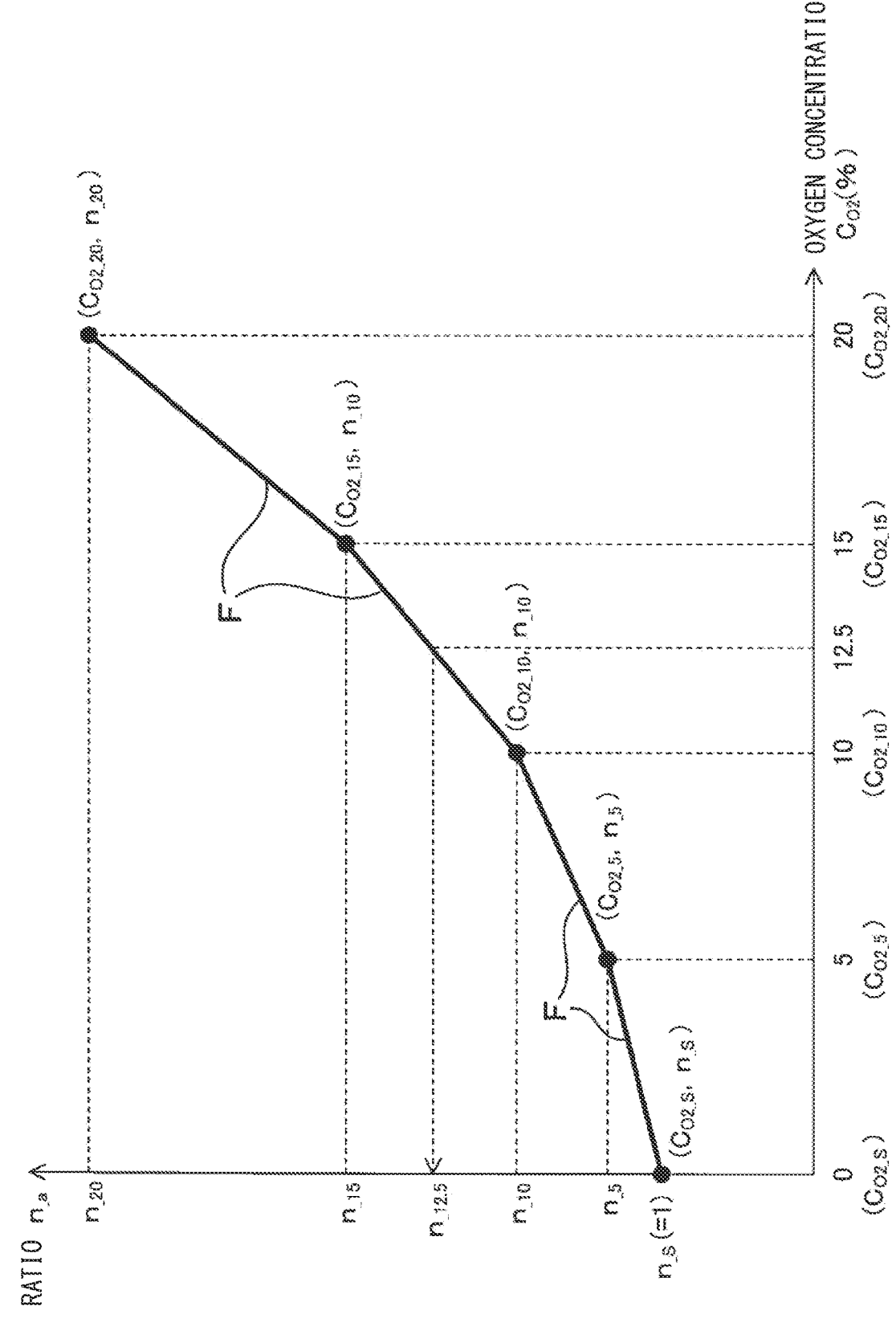
FIG. 7 is a graph showing a ratio $n_{-a}$ when the oxygen concentration $C_{O2}$ takes a discrete value and a complementary function according to the first embodiment.

Further, the computation unit 4 computes the inclination $\gamma$ by using a predetermined complementary function F, when the oxygen concentration $C_{O2}$ is neither the oxygen reference value $C_{O2\_S}$ nor the discrete value $C_{O2\_a}$. More specifically, as shown in FIG. 7, the computation unit 4 stores the ratio $n_{\_a}$ when the oxygen concentration $C_{O2}$ takes the discrete value $C_{O2\_a}$ and the ratio $n_{\_S}$ (that is, 1) when the oxygen concentration $C_{O2}$ takes the oxygen reference value $C_{O2\_S}$. Further, the computation unit 4 stores, as the complementary function F, a straight line connecting the points (that is, ($C_{O2\_S}$, $n_{\_S}$) or ($C_{O2\_a}$, $n_{\_a}$)) formed of a combination of the oxygen concentration $C_{O2}$ and the ratio $n_{\_a}$.

The computation unit 4 uses this complementary function F to compute the corresponding ratio n, when the oxygen concentration $C_{O2}$ is neither the oxygen reference value $C_{O2\_S}$ nor the discrete value $C_{O2\_a}$. For example, when the measured oxygen concentration $C_{O2}$ is 12.5%, the complementary function F is used to compute the corresponding ratio $n_{\_12.5}$. Then, this ratio $n_{\_12.5}$ is multiplied by the inclination $\gamma_{\_S}$ of the above equation (2). That is, the following equation $$I = n_{\_12.5}\gamma_{\_S}C_{NOX}$$

is derived. In this way, the above equation (1) when the oxygen concentration $C_{O2}$ is 12.5% is specified, and the specific gas concentration $C_{NOX}$ is computed by using this equation (1).

Next, a method of manufacturing the gas concentration measuring device will be described. In this embodiment, a sensor manufacturing process for manufacturing the gas sensor 2 and a calibration process are performed. In the calibration process, the gas sensor 2 is exposed to the reference gas, and the measured value $I_{\_S}$ of the sensor current I is acquired. Subsequently, the measured value $I_{\_S}$ is stored in the computation unit 4.

Figure 8:
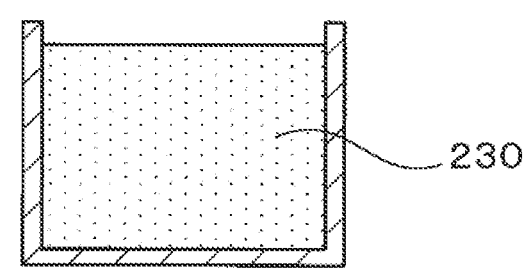
FIG. 8 is an explanatory view showing a manufacturing method for the gas sensor according to the first embodiment.
Figure 8:
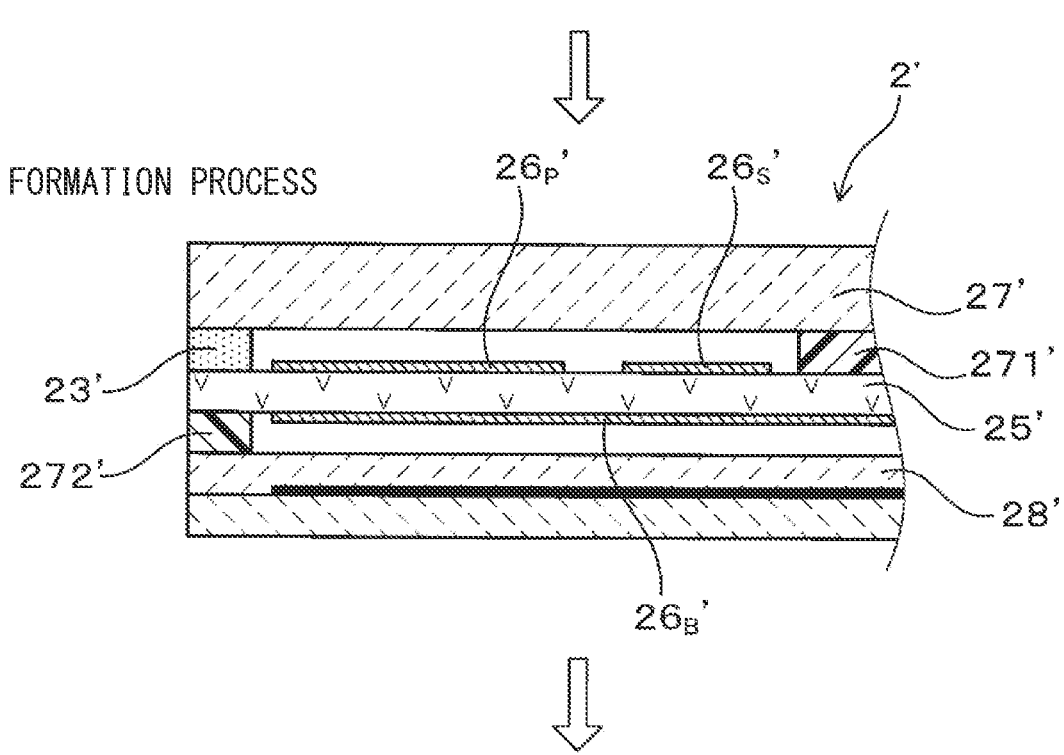
Figure 8:
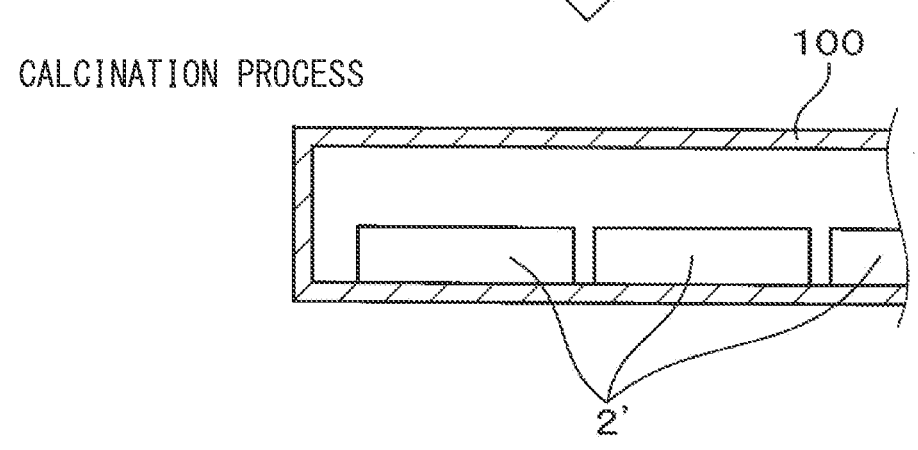

As shown in FIG. 8, in the sensor manufacturing process, a material production process, a formation process, and a calcination process are performed. In the material production process, a non-calcinated material 230 of the diffusion resistance portion 23 is manufactured. For example, the non-calcinated material 230 is produced by adding a binder to ceramic powder and mixing the binder and the ceramic powder. Further, a non-calcinated material of the insulating plates 27 and 28, a non-calcinated material of the solid electrolyte body 25, and the like are also manufactured.

After the material production process, a formation process is performed. In the formation process, the non-calcinated material 230 is formed in a predetermined shape to produce a non-calcinated body 23' of the diffusion resistance portion 23. In this example, multiple non-calcinated bodies 23' are manufactured by using the non-calcinated material 230 produced in the material production process. Further, by using the non-calcinated materials of the solid electrolyte body 25 and the insulating plates 27 and 28, the non-calcinated body 25' of the solid electrolyte body 25, the non-calcinated bodies 27' and 28' of the insulating plates 27 and 28, and the like are also formed. Subsequently, the non-calcinated electrode 26$_{S'}$ of the sensor electrode 26$_S$, the non-calcinated electrode 26$_{P'}$ of the pump electrode 26$_P$, the non-calcinated electrode 26$_{B'}$ of the reference electrode 26B, and a conductive wire as a lead wire thereof are formed by screen printing or the like on the surface of the non-calcinated body 25' of the solid electrolyte body 25. Further, a heater and its lead wire are formed on one insulating layer of the insulating plate 28', which includes two insulating layers, by screen printing or the like. On the other hand, a non-calcinated body 271' corresponding to the partition wall portion 271 is formed with a surrounded space that forms the measured gas chamber 21. The non-calcinated body 23' of the diffusion resistance portion 23 described above is arranged in a notch portion corresponding to the entrance of this space. Subsequently, these are laminated. In this way, the non-calcinated body 2' of the gas sensor 2 is produced.

Subsequently, a calcination process is performed. In the calcination process, multiple non-calcinated bodies 2' of the gas sensor 2 are accommodated in a calcination furnace 100. Subsequently, the multiple non-calcinated bodies 2' are heated to a predetermined temperature. By performing the calcination process, the non-calcinated body 23' of the diffusion resistance portion 23 and the like are calcinated, and the gas sensor 2 is manufactured.

After manufacturing the gas sensor 2, the above calibration process is performed. Herein, the computation unit 4 is connected to the gas sensor 2 (see FIG. 6), and the gas sensor 2 is exposed to the reference gas (that is, gas in which the specific gas concentration $C_{NOX}$ and the oxygen concentration $C_{O2}$ are adjusted to predetermined values). Subsequently, the sensor current I is actually measured, and the measured value $I_{\_S}$ is stored in the computation unit 4. In this way, a manufacturing variation in the characteristics (S, L, β) of the diffusion resistance portion 23 is corrected. For example, in the calibration process, the specific gas concentration $C_{NOX}$ is common, and the calibration is performed by using two reference gases having an oxygen concentration $C_{O2}$ of 0% and 20%.

Further, in the present embodiment, multiple gas sensors 2, on which the material production process or the calcination process has been performed at the same time, are classified as one lot, and the measured value $I_{\_S}$ is measured and stored for each lot. That is, the multiple gas sensors 2 using the non-calcinated material 230 produced in the same material production process or the multiple gas sensors 2 calcinated in the same calcination process are classified as one lot. Subsequently, one of the gas sensors 2 is selected from this lot, and the measured value $I_{\_S}$ is measured and stored in the computation unit 4. The same measured value $I_{\_S}$ is also stored in another gas sensor 2 of the same lot. As for the lot, a predetermined period may be set in advance, and the period may be used to classify the one lot. For example, multiple gas sensors 2 on the same manufacturing date may be classified as one lot. Alternatively, in a case where the material used for the diffusion resistance unit 23 of the gas sensor 2 is switched to an equivalent material (that is, the material having the same composition but having a different material property), the period between the switchings may be used to classify the one lot.

The operation effect of the embodiment will be described. The gas concentration measuring device 1 of the present embodiment includes the oxygen concentration measuring unit 3 and the computation unit 4. The computation unit 4 computes the specific gas concentration $C_{NOX}$ by using the measured value of the oxygen concentration $C_{O2}$ with the oxygen concentration measuring unit 3 and the measured value of the current (that is, the sensor current I) of the sensor cell 24$_S$.

Therefore, when the specific gas concentration $C_{NOX}$ is computed, the information on the oxygen concentration $C_{O2}$ in the measured gas can be reflected. Therefore, the specific gas concentration $C_{NOX}$ can be accurately acquired without being significantly affected by the oxygen concentration $C_{O2}$.

Further, the computation unit 4 of this embodiment computes the specific gas concentration $C_{NOX}$ by using the above equation (1). The above equation (1) is an equation that accurately expresses the relationship between the oxygen concentration $C_{O2}$, the specific gas concentration $C_{NOX}$, and the sensor current I. Therefore, by using this equation (1), the specific gas concentration $C_{NOX}$ can be computed more accurately. In addition, by using the equation representing the physical event, in a case where multiple reference gases are used, the configuration enables to perform more accurate correction than a configuration simply performing an approximate correction of the oxygen concentration $C_{O2}$.

Further, the above equation (1), in a case where the oxygen concentration $C_{O2}$ is a constant value, is expressed by the following equation in which the inclination of the linear function is γ.

$$I = \gamma C N_{OX}$$

The computation unit 4 computes the inclination γ, in a case where the oxygen concentration $C_{O2}$ takes a constant value other than the oxygen reference value $C_{O2\_S}$, by using the reference equation represented by the above equation (2). In this way, the above equation (1) is derived, and the configuration computes the specific gas concentration $C_{NOX}$ by using this equation (1). The configuration enables to reduce the load on the computation unit 4 in this way. That is, the above equation (1) includes a logarithm. Therefore, n a case where the equation (1) is used as it is, a large load is applied to the computation unit 4. Therefore, the computation unit 4 is required to have a high computation speed, and the computation unit 4 may become large in size. To the contrary, the equation (1) is transformed into $I=\gamma C_{NOX}$, and the inclination γ is computed by using the reference equation, and therefore, the configuration does not require to compute the logarithm or the like. Therefore, the equation (1) can be easily derived in a case where the oxygen concentration $C_{O2}$ takes a value other than the oxygen reference value $C_{O2\_S}$. Therefore, the configuration enables to reduce the load on the computation unit 4. Further, the configuration does not require the computation unit 4 to increase its size or its cost in order to improve the computation speed.

Further, the computation unit 4 stores the actually measured value $I_{\_S}$ of the sensor current I when the reference gas is used. The above equation (2) is defined by using this actually measured value $I_{\_S}$.

Therefore, the configuration enables to correct the variation in the characteristics (S, L, β) of the diffusion resistance unit 23 for each gas sensor 2 and to accurately compute the specific gas concentration $C_{NOX}$.

Further, the computation unit 4 of the present embodiment stores the ratio $n_{\_a}$ computed in advance by using the above equation (3). Further, the inclination $\gamma_{\_S}$ of the reference equation is multiplied by the ratio $n_{\_a}$, and the equation (1) (that is, $I=n_{\_a}\gamma_{\_S}C_{NOX}$) when the oxygen concentration $C_{O2}$ is the discrete value $C_{O2\_a}$ is derived.

The ratio $n_{\_a}$ is not affected by the manufacturing variation of the gas sensor 2 and is constant in all the gas sensors 2. Therefore, by multiplying the above-mentioned reference equation, which reflects the manufacturing variation of the gas sensor 2, by the ratio $n_{\_a}$, the equation (1) when the oxygen concentration $C_{O2}$ takes the discrete value $C_{O2\_a}$ can be easily derived. Therefore, the configuration enables to reduce the load on the computation unit 4.

Further, the computation unit 4 of the present embodiment computes the inclination γ by using the above-described complementary function F (see FIG. 7), when the oxygen concentration $C_{O2}$ is neither the oxygen reference value $C_{O2\_S}$ nor the discrete value $C_{O2\_a}$. In this way, the equation (1) in this case is derived.

In this way, the equation (1) can be accurately derived even when the oxygen concentration $C_{O2}$ is neither the oxygen reference value $C_{O2\_S}$ nor the discrete value $C_{O2\_a}$. In this embodiment, the complementary function F is a straight line, however, it is noted that, the present embodiment is not limited to this, and the complementary function F may be a curved line.

Further, in the manufacturing method of the gas concentration measuring device 1 in this embodiment, the sensor manufacturing process and the calibration process are performed. As shown in FIG. 8, in the sensor manufacturing process, the material production process, the formation process, and the calcination process are performed. In the calibration process, multiple gas sensors 2, on which the material production process or the calcination process have been performed at the same time, are classified as one lot. The measured value $I_{\_S}$ is acquired by using one gas sensor 2 selected from the lot. Subsequently, the measured value $I_{\_S}$ is stored in the computation unit 4 connected to the gas sensor 2 of the lot.

The characteristics of the diffusion resistance portions 23 of the multiple gas sensors 2, on which the material production process or the calcination process is performed at the same time, are substantially equal to each other. Therefore, by selecting one gas sensor 2 and acquiring the measured value $I_{\_S}$, this measured value $I_{\_S}$ can be used for another gas sensor 2 of the same lot. Thus, it is not necessary to acquire the measured value $I_{\_S}$ for all the gas sensors 2, and the gas concentration measuring device 1 can be easily manufactured.

As described above, according to this embodiment, the configuration enables to provide the gas concentration measuring device configured to measure the specific gas concentration contained in the measured gas more accurately.

In other words, the gas concentration measuring device 1 of the present embodiment as described above is configured to measure the concentration of the specific gas based on the following concept.

The computation unit 4 acquires the coefficient γ from the oxygen concentration $C_{O2}$ with the oxygen concentration measurement unit 3. The coefficient γ is the coefficient that is set such that the value increases as the oxygen concentration increases.

Further, by using equation using the coefficient γ and the measured sensor current I, $$C_{NOX}=I/\gamma \qquad (1\text{-}1)$$

the computation unit 4 computes the concentration $C_{NOX}$ of the specific gas.

In other words, the gas concentration measuring device 1 of the present embodiment is configured to measure the concentration of the specific gas based on the following concept.

The relationship between the sensor current I and the concentration $C_{NOX}$ of the specific gas for the specific gas sensor 2 is as follows.

$$I=\gamma C_{NOX} \qquad (1\text{-}1)$$

γ is a coefficient determined according to the oxygen concentration $C_{O2}$.

When the oxygen concentration $C_{O2}$ is the reference oxygen reference value $C_{O2\_S}$, γ at this time is $\gamma_{\_S}$, and the above equation (1-1) is shown as follows.

$$I=\gamma_{\_S}C_{NOX} \qquad (2)$$

$\gamma_{\_S}$ is acquired from $\gamma_{\_S}=I_{\_S}/C_{NOX}$ by substituting the specific gas reference value $C_{NOX\_}S$, which is the predetermined specific gas concentration, and the measured value $I_{\_S}$ of the sensor current, when the gas sensor 2 is exposed to the specific gas having the specific gas reference value, into $C_{NOX}$ and I in the above equation (2), respectively.

Including the case where the above oxygen concentration $C_{O2}$ is other than the above oxygen reference value $C_{O2\_S}$, the γ is determined by multiplying $\gamma_{\_S}$ by the ratio n, which is specified according to the oxygen concentration $C_{O2}$ based on the predetermined complementary function F, that is, $\gamma=n\gamma_S$.

By applying this value of γ to the above equation (1-1), the concentration $C_{NOX}$ of the specific gas is computed from the equation (1-1).

As described above, in the technical field of the gas concentration measuring device, an issue arises that as the oxygen concentration in the measured gas becomes higher, the specific gas concentration in the measured gas chamber becomes higher. In order to address this issue, the above-mentioned computation unit for computing the concentration of the specific gas is caused to perform the correction such that as the oxygen concentration in the measured gas becomes higher, the actually measured sensor current I becomes smaller. In this way, the configuration enables to measure the concentration of the specific gas contained in the measured gas more accurately.

Among reference numerals used in the subsequent embodiments, the same reference numerals as those used in the first embodiment represent the same components as those in the first embodiment, unless otherwise indicated.

Second Embodiment

Figure 9:
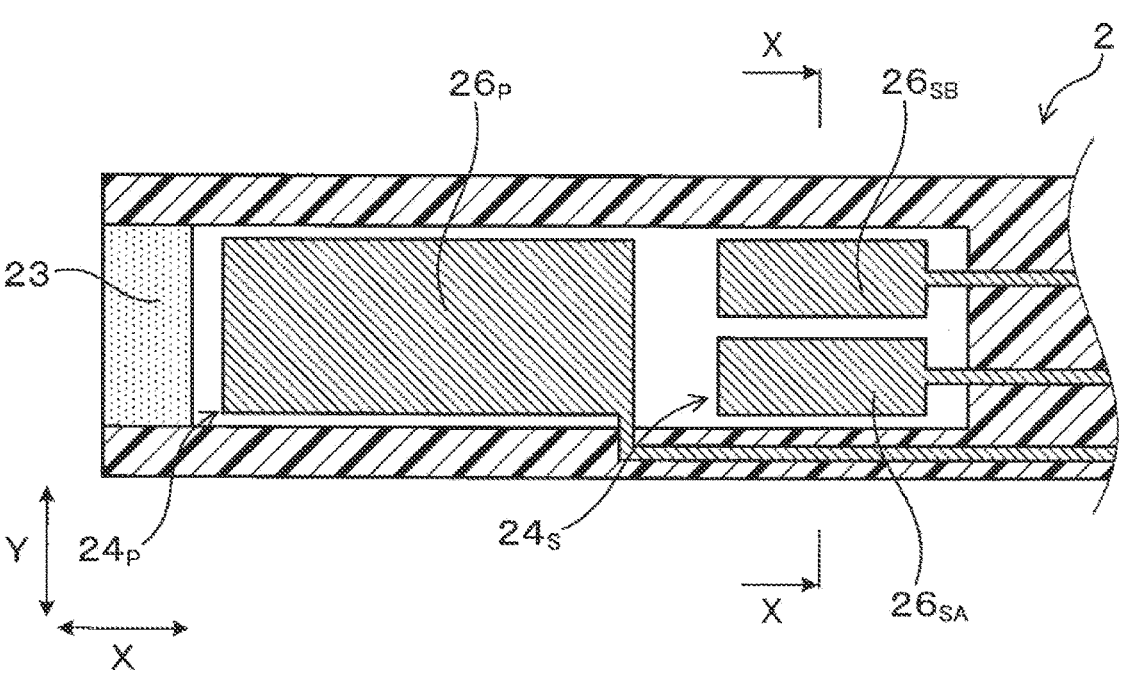
FIG. 9 is a cross-sectional view showing a gas sensor according to a second embodiment.
Figure 10:
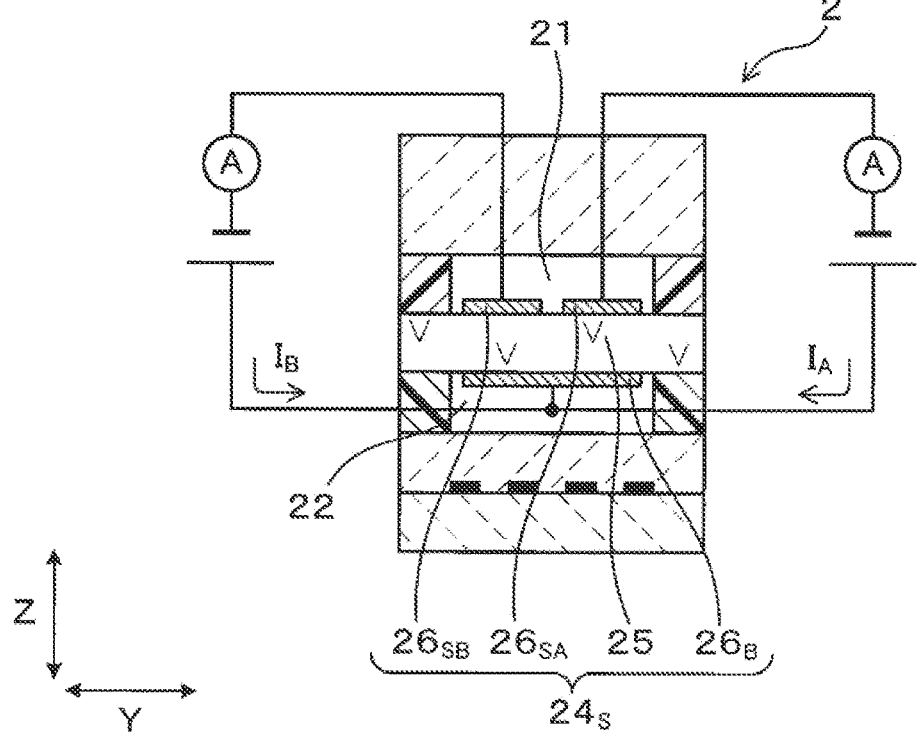
FIG. 10 is a cross-sectional view taken along a line X-X in FIG. 9.

The embodiment is an example in which the structure of the gas sensor 2 is modified. As shown in FIGS. 9 and 10, the gas sensor 2 of this embodiment includes two sensor electrodes $26_S$ including a first sensor electrode $26_{SA}$ and a second sensor electrode $26_{SB}$. The first sensor electrode $26_{SA}$ contains Pt and Rh. The first sensor electrode $26_{SA}$ is active to oxygen and NOx. Further, the second sensor electrode $26_{SB}$ contains Au and Pt. The second sensor electrode $26_{SB}$ is active only to oxygen.

In this embodiment, similarly to the first embodiment, the pump cell $24_P$ is used to discharge oxygen from the measured gas chamber 21. However, oxygen may not be completely discharged, and a small amount of oxygen may remain. The first sensor electrode $26_{SA}$ is active to NOx and oxygen, and therefore, a current $I_A$ corresponding to the total concentration of NOx and oxygen flows through the first sensor electrode $26_{SA}$. Further, the second sensor electrode $26_{SB}$ is active only to oxygen, and therefore, a current $I_B$ corresponding to the oxygen concentration flows through the second sensor electrode $26_{SB}$. In this embodiment, as shown in the following equation, a value acquired by subtracting the current $I_B$ of the second sensor electrode $26_{SB}$ from the current $I_A$ of the first sensor electrode $26_{SA}$ is defined as the sensor current I.

$$I=I_A-I_B$$

Then, the computed sensor current I is used to compute the concentration $C_{NOX}$ of NOx (that is, the specific gas). As the computation method after computing the sensor current I, the same method as in the first embodiment is adopted.

The configuration enables to compute the specific gas concentration $C_{NOX}$ accurately even when oxygen cannot be completely discharged by using the pump cell 24P.

The present embodiment has similar configurations and produces similar operation effects to those in the first embodiment.

Third Embodiment

Figure 11:
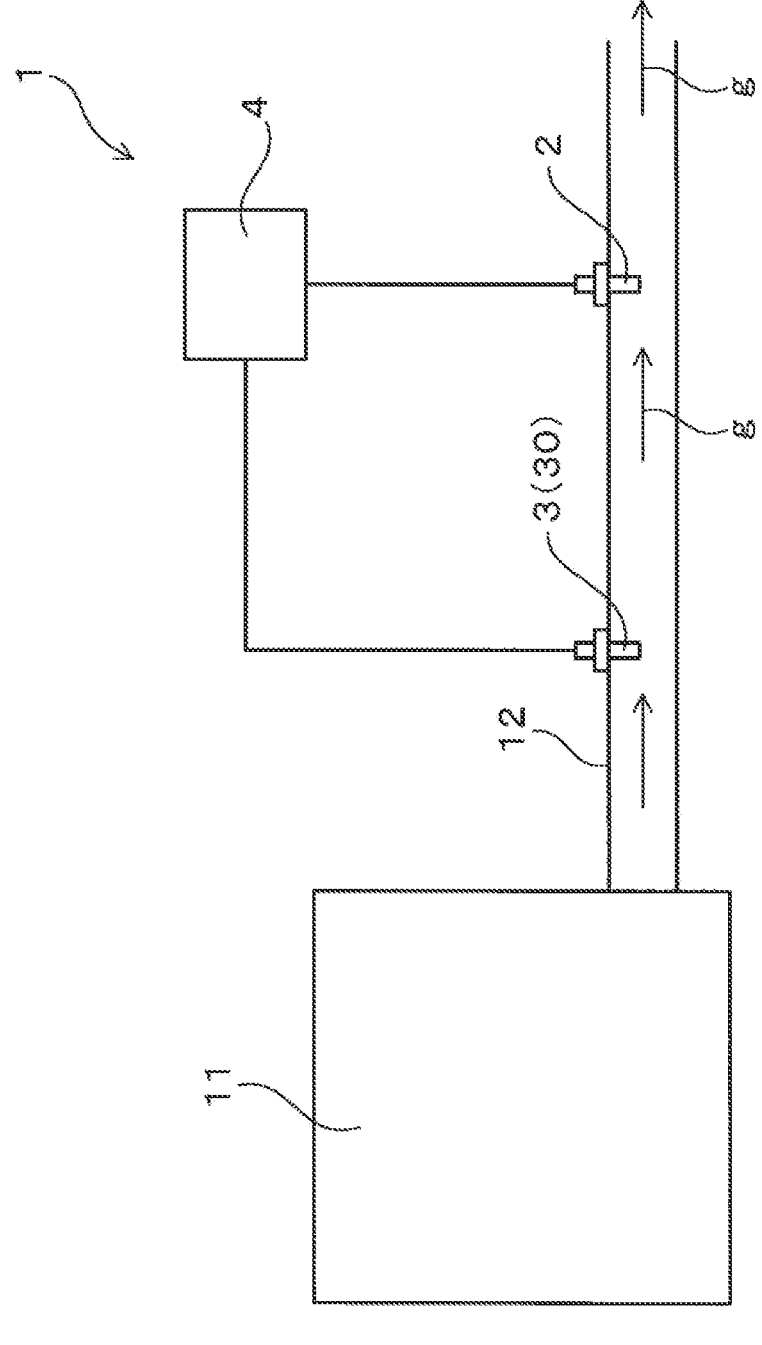
FIG. 11 is a schematic diagram showing a gas concentration measuring device according to a third embodiment.

This embodiment is an example in which the configuration of the oxygen concentration measuring unit 3 is modified. As shown in FIG. 11, in this embodiment, an NF sensor 30 is arranged in the vicinity of the gas sensor 2. The oxygen concentration $C_{O2}$ in the measured gas g is measured by using this A/F sensor 30. That is, in this embodiment, the NF sensor 30 is used as the oxygen concentration measuring unit 3.

The present embodiment has similar configurations and produces similar operation effects to those in the first embodiment.

In this embodiment, the oxygen concentration $C_{O2}$ is measured by using the A/F sensor 30, however, the present disclosure is not limited to this. Specifically, for example, an oxygen sensor may be arranged in the vicinity of the gas sensor 2, and the oxygen sensor may be used to measure the oxygen concentration $C_{O2}$ in the measured gas g.

The present disclosure is not limited to the respective embodiments described above, and various modifications may be adopted within the scope of the present disclosure without departing from the spirit of the disclosure.

For example, in the above-described embodiments, the computation unit 4 is provided in the sensor control unit connected to the gas sensor 2. However, the present disclosure is not limited to this, and the computation unit 4 may be provided in an ECU (engine control unit) that controls the engine. In this case, a part of a function of the sensor control unit may be assigned to the ECU, and the sensor control unit can be downsized.

Further, in the first embodiment and the second embodiment, the pump cell 24P is used as the oxygen concentration measuring unit 3. It is noted that, a second pump cell may be provided between the pump cell $24_P$ and the sensor cell $24_S$ in the flow direction of the measured gas, that is, in the X direction, and may be used as the oxygen concentration measuring unit 3.

Although the present disclosure has been described in accordance with the embodiments, it is understood that the present disclosure is not limited to such embodiments or structures. The present disclosure encompasses various modifications and variations within the scope of equivalents. In addition, while the various elements are shown in various combinations and configurations, which are exemplary, other combinations and configurations, including more, less or only a single element, are also within the spirit and scope of the present disclosure.

What is claimed is:

1. A gas concentration measuring device, comprising:
a gas sensor configured to measure a concentration $C_{NOX}$ of specific gas contained in measured gas;
an oxygen concentration measuring unit configured to measure a concentration $C_{O2}$ of oxygen in the measured gas; and
a computation unit configured to compute the concentration $C_{NOX}$ of the specific gas,
wherein
the gas sensor includes:
a measured gas chamber into which the measured gas is to be introduced,
a reference gas chamber into which reference gas is to be introduced,
a diffusion resistance unit configured to regulate a flow velocity of the measured gas to be introduced into the measured gas chamber,
a pump cell configured to move oxygen from the measured gas chamber into the reference gas chamber, and
a sensor cell configured to cause a sensor current I to flow therethrough correspondingly to the concentration $C_{NOX}$ of the specific gas in the measured gas chamber, wherein
the computation unit is configured to compute the concentration $C_{NOX}$ of the specific gas by using a measured value of the concentration $C_{O2}$ of oxygen with the oxygen concentration measuring unit and a measured value of the sensor current I,
the gas concentration measuring device is configured for mounting on a vehicle, the gas sensor is configured to be operatively coupled to an exhaust pipe, the gas sensor is configured to measure the concentration $C_{NOX}$ contained in exhaust gas emitted from the exhaust pipe, and the computed concentration $C_{NOX}$ of the specific gas is used in association with the gas sensor,
an area of the diffusion resistance unit on a plane orthogonal to an introduction direction of the measured gas is S,
a length of the diffusion resistance unit in the introduction direction is L,
pressure of the measured gas outside the gas sensor is P,
temperature of the diffusion resistance unit is T,
a diffusion coefficient of the measured gas is D, and
A and β are constants, wherein
the computation unit is configured to compute the concentration $C_{NOX}$ of the specific gas by using the measured value of the concentration $C_{O2}$ of oxygen and the measured value of the sensor current I and by using the equation (1)

(equation (1))

$$I = A\frac{P}{T}\frac{S}{L}C_{NOX}\left\{D + \frac{1}{\beta}P\ C_{O2}\ln(1 - C_{O2})\right\}. \tag{1}$$

2. The gas concentration measuring device according to claim 1,
wherein
the equation (1), when the concentration $C_{O2}$ of oxygen is a constant value, is expressed by the following equation in which an inclination of its linear function is γ, $$I = \gamma C_{NOX}$$

the computation unit is configured to store a measured value Is of the sensor current I in a state where the concentration $C_{NOX}$ of the specific gas is a predetermined specific gas reference value $C_{NOX}$ s and where the concentration $C_{O2}$ of oxygen is a predetermined oxygen reference value $C_{O2\_S}$, and
the computation unit is configured to compute the inclination γ when the concentration $C_{O2}$ of oxygen is the constant value other than the oxygen reference value $C_{O2}$ s by using a reference equation that is the following equation (2) and that defines a relationship between the sensor current I and the concentration $C_{NOX}$ of the specific gas, when the concentration $C_{O2}$ of oxygen is the oxygen reference value $C_{O2}$ s, to derive the equation (1)

(equation (2))

$$I = \gamma_{\_S}C_{NOX} \tag{2}$$

$$\gamma_{\_S} = \frac{I_{\_S}}{C_{NOX\_S}}.$$

3. The gas concentration measuring device according to claim 2, wherein
the computation unit is configured to store a ratio n a of the sensor current I, when the concentration $C_{O2}$ of oxygen is a predetermined discrete value $C_{O2\_a}$ other than the oxygen reference value $C_{O2\_S}$, to the reference equation,
the ratio $n_{\_a}$ is computed in advance by using the following equation (3), and (equation (3))

$$n_{\_a} = \frac{I(C_{O2\_a})}{I(C_{O2\_S})}$$

$$= \frac{A\frac{P}{T}\frac{S}{L}C_{NOX}\left\{D + \frac{1}{\beta}PC_{O2\_a}\ln(1 - C_{O2\_a})\right\}}{A\frac{P}{T}\frac{S}{L}C_{NOX}\left\{D + \frac{1}{\beta}PC_{O2\_S}\ln(1 - C_{O2\_S})\right\}}$$

(3)

the computation unit is configured to multiply the ratio $n_{\_a}$ by the inclination $\gamma_{\_S}$ of the reference equation to derive the equation (1) when the concentration $C_{O2}$ of oxygen is the discrete value $C_{O2\_a}$.

4. The gas concentration measuring device according to claim 3, wherein the computation unit is configured to compute the inclination $\gamma$ by using a predetermined complementary function to derive the equation (1) when the concentration $C_{O2}$ of oxygen is neither the oxygen reference value $C_{O2}$ s nor the discrete value $C_{O2\_a}$.

5. The gas concentration measuring device according to claim 3, wherein the ratio $n_{\_a}$ is a ratio of the sensor current I, when the concentration $C_{O2}$ of oxygen is the predetermined discrete value $C_{O2}$ a other than the oxygen reference value $C_{O2\_S}$, to the sensor current I when the concentration $C_{O2}$ of oxygen is the oxygen reference value $C_{O2\_S}$ in the reference equation.

6. A method for manufacturing the gas concentration measuring device according to claim 3, comprising:

manufacturing the gas sensor in a sensor manufacturing process; and measuring a measured current value $I_{\_S}$ and causing the computation unit to store the measured current value $I_{\_S}$ in a calibration process, wherein the sensor manufacturing process includes producing a non-calcinated material of the diffusion resistance unit in a material production process and calcinating the produced non-calcinated material in a calcinating process, the calibration process includes acquiring the measured current value $I_{\_S}$ by using the gas sensor of a plurality of gas sensors selected from a lot, wherein the plurality of gas sensors, on which the material production process or the calcination process have been performed at the same time, are classified as the lot, and the computation unit, which is connected to the gas sensor of the lot, is caused to store the measured current value $I_{\_S}$ subsequently.

7. The gas concentration measuring device according to claim 1, wherein the computation unit is configured to acquire a coefficient $\gamma$, which is set such that its value increases as the concentration of oxygen increases, from the concentration $C_{O2}$ of oxygen measured by using the oxygen concentration measuring unit and compute the concentration $C_{NOX}$ of the specific gas by using an equation of $C_{NOX}=I/\gamma$ that uses the coefficient $\gamma$ and the measured value of the sensor current I.

8. The gas concentration measuring device according to claim 1, wherein a relationship between the sensor current I and the concentration $C_{NOX}$ of the specific gas of the gas sensor is as follows, $$I=\gamma C_{NOX}$$ (1-1)

wherein $\gamma$ is a coefficient determined according to the concentration $C_{O2}$ of oxygen, when the concentration $C_{O2}$ of oxygen is an oxygen reference value $C_{O2\_S}$, $\gamma$ is $\gamma_{\_S}$, and the equation (1-1) is as follows, $$I=\gamma_{\_S}C_{NOX}$$ (2)

wherein $\gamma_{\_S}$ is acquired from $Y_{\_S}=I_{\_S}/C_{NOX}$ by substituting a reference value $C_{NOX\_S}$ of the specific gas, which is a predetermined specific gas concentration, and a measured value $I_{\_S}$ of the sensor current, when the gas sensor is exposed to the specific gas at the specific gas reference value, into $C_{NOX}$ and I in the equation (2), respectively, when the concentration $C_{O2}$ of oxygen is other than the oxygen reference value $C_{O2\_S}$, $\gamma$ is determined by multiplying $\gamma_{\_S}$ by a ratio n, which is specified according to the concentration $C_{O2}$ of oxygen based on a predetermined complementary function, as follows, and $$\gamma=n\gamma_{\_S}$$

the concentration $C_{NOX}$ of the specific gas is computed from the equation (1-1) and by substituting the value of $\gamma$ to the equation (1-1).

9. The gas concentration measuring device according to claim 1, wherein the computation unit is configured to be provided in an engine control unit (ECU), wherein the ECU is configured to control an engine.

10. The gas concentration measuring device according to claim 1, wherein the computation unit is provided in a sensor control unit and the sensor control unit is electrically connected to the gas sensor.

11. The gas concentration measuring device according to claim 1, wherein the computation unit includes, at least, an arithmetic processing unit and a storage device.

12. The gas concentration measuring device according to claim 11, wherein the computation unit stores the measured value of the sensor current I in the storage device.

13. The gas concentration measuring device according to claim 12, wherein a manufacturing variation of the diffusion resistance unit is corrected.

14. The gas concentration measuring device according to claim 1, wherein the equation (1), when the concentration $C_{O2}$ of oxygen is a constant value, is expressed by the following equation in which an inclination of its linear function is $\gamma$, $$I=\gamma C_{NOX}, \text{ and}$$

the computation unit is configured to store a measured value $I_{\_S}$ of the sensor current I in a state where the concentration $C_{NOX}$ of the specific gas is a predetermined specific gas reference value $C_{NOX\_S}$ and where the concentration $C_{O2}$ of oxygen is a predetermined oxygen reference value $C_{O2\_S}$.

15. The gas concentration measuring device according to claim 1, wherein only the measured value of the concentration $C_{O2}$ of oxygen and the concentration $C_{NOX}$ of the specific gas are variable values in equation (1).

16. A gas concentration measuring device, comprising:

a gas sensor configured to measure a concentration $C_{NOX}$ of specific gas contained in measured gas;

an oxygen concentration measuring unit configured to measure a concentration $C_{O2}$ of oxygen in the measured gas; and a computation unit configured to compute the concentration $C_{NOX}$ of the specific gas, wherein the gas sensor includes:

a measured gas chamber into which the measured gas is to be introduced, a reference gas chamber into which reference gas is to be introduced, a diffusion resistance unit configured to regulate a flow velocity of the measured gas to be introduced into the measured gas chamber, a pump cell configured to move oxygen from the measured gas chamber into the reference gas chamber, and a sensor cell configured to cause a sensor current I to flow therethrough correspondingly to the concentration $C_{NOX}$ of the specific gas in the measured gas chamber, wherein the computation unit is configured to compute the concentration $C_{NOX}$ of the specific gas by using a measured value of the concentration $C_{O2}$ of oxygen with the oxygen concentration measuring unit and a measured value of the sensor current I, an area of the diffusion resistance unit on a plane orthogonal to an introduction direction of the measured gas is S, a length of the diffusion resistance unit in the introduction direction is L, pressure of the measured gas outside the gas sensor is P, temperature of the diffusion resistance unit is T, a diffusion coefficient of the measured gas is D, and A and β are constants, wherein the computation unit is configured to compute the concentration $C_{NOX}$ of the specific gas by using the measured value of the concentration $C_{O2}$ of oxygen and the measured value of the sensor current I and by using the equation (1), (equation (1))

$$I = A\ P/T\ S/L\ C_{NOX}[D + 1/\beta P\ C_{O2} \ln(1 - C_{O2})] \qquad (1)$$

\* \* \* \* \*